(12) United States Patent
Jensen et al.

(10) Patent No.: US 6,716,394 B2
(45) Date of Patent: *Apr. 6, 2004

(54) DNA SEQUENCING USING MULTIPLE FLUORESCENT LABELS BEING DISTINGUISHABLE BY THEIR DECAY TIMES

(75) Inventors: Morten Jensen, San Francisco, CA (US); J. Wallace Parce, Palo Alto, CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/179,686

(22) Filed: Jun. 24, 2002

(65) Prior Publication Data

US 2003/0036080 A1 Feb. 20, 2003

Related U.S. Application Data

(63) Continuation of application No. 09/213,297, filed on Dec. 15, 1998, now Pat. No. 6,447,724, which is a continuation-in-part of application No. 09/132,181, filed on Aug. 11, 1998, now abandoned.
(60) Provisional application No. 60/122,064, filed on Aug. 11, 1998.

(51) Int. Cl.$^7$ .................. G01N 15/06; C12Q 1/68
(52) U.S. Cl. .................. 422/68.1; 435/6; 55/58; 55/82.05; 55/99
(58) Field of Search .................. 422/68.1; 435/6; 55/58, 82.05, 99

(56) References Cited

U.S. PATENT DOCUMENTS

| 4,084,905 A | 4/1978 | Schreiber et al. |
| 4,118,619 A | 10/1978 | McArthur et al. |
| 4,341,957 A | 7/1982 | Wieder |

(List continued on next page.)

FOREIGN PATENT DOCUMENTS

| EP | 556509 | 8/1993 |
| EP | 617286 | 9/1994 |
| EP | 753584 | 1/1997 |

(List continued on next page.)

OTHER PUBLICATIONS

Jameson, David M. et al. Methods in Enzymology, vol. 278 (1997) "Fluorescent Nucleotide Analogs: Synthesis and Applications" pp. 363–390.

Terpetschnig, Ewald et al., Methods in Enzymology vol. 278 (1997) Long–Lifetime Metal–Ligand Complexes as Probes in Biophysics and Clinical Chemistry pp. 295–321.

Voss et al.; "Direct genomic fluorescent on–line sequencing and analysis using in vitro amplification of DNA"; *Nucleic Acids Research,* vol. 17, No. 7 (1989), pp. 2517–2527.

Tong et al.; "Simple double–beam absorption detection systems for capillary electrophoresis based on diode lasers and light–emitting diodes"; *Journal of Chromatography A,* 718 (1995) pp. 177–185.

(List continued on next page.)

*Primary Examiner*—Jezia Riley
(74) *Attorney, Agent, or Firm*—Donald R. McKenna; Quine Intellectual Property Law Group

(57) ABSTRACT

A method is provided for identifying components of a mixture by labeling the individual components with fluorescent agents having different fluorescence lifetimes. The components are subsequently separated, fluorescent labels detected and their lifetimes measured. Based on the measured fluorescent lifetimes, the components of mixtures of small organic molecules, polymers, peptides, saccharides and nucleic acids can be identified.

6 Claims, 1 Drawing Sheet

U.S. PATENT DOCUMENTS

| | | |
|---|---|---|
| 4,483,614 A | 11/1984 | Rogers |
| 4,675,300 A | 6/1987 | Zare et al. |
| 4,683,579 A | 7/1987 | Wardlaw |
| 4,849,513 A | 7/1989 | Smith et al. |
| 4,855,225 A | 8/1989 | Fung et al. |
| 4,945,245 A | 7/1990 | Levin |
| 4,962,045 A | 10/1990 | Picozza et al. |
| 5,047,519 A | 9/1991 | Hobbs, Jr. et al. |
| 5,171,534 A | 12/1992 | Smith et al. |
| 5,485,530 A | 1/1996 | Lakowicz et al. |
| 5,504,337 A | 4/1996 | Lakowicz et al. |
| 5,556,790 A | 9/1996 | Pettit |
| 5,626,134 A | 5/1997 | Zuckerman |
| 5,699,157 A | 12/1997 | Parce |
| 5,720,928 A | 2/1998 | Schwartz |
| 5,759,374 A | 6/1998 | Takahashi et al. |
| 5,770,029 A | 6/1998 | Nelson et al. |
| 5,779,868 A | 7/1998 | Parce et al. |
| 5,800,690 A | 9/1998 | Chow et al. |
| 5,842,787 A | 12/1998 | Kopf-Sill et al. |
| 5,852,495 A | 12/1998 | Parce |
| 5,869,004 A | 2/1999 | Parce et al. |
| 5,876,675 A | 3/1999 | Kennedy |
| 5,880,071 A | 3/1999 | Parce et al. |
| 5,882,465 A | 3/1999 | McReynolds |
| 6,049,380 A | 4/2000 | Goodwin et al. |
| 6,447,724 B1 * | 9/2002 | Jensen et al. ............ 422/68.1 |

FOREIGN PATENT DOCUMENTS

| | | |
|---|---|---|
| EP | 971038 | 1/2000 |
| WO | WO 90/00623 | 1/1990 |
| WO | WO 94/18218 | 8/1994 |
| WO | WO 96/27798 | 9/1996 |
| WO | WO 98/00231 | 1/1998 |
| WO | WO 98/05424 | 2/1998 |
| WO | WO 98/09154 | 3/1998 |
| WO | WO 98/22811 | 5/1998 |
| WO | WO 98/32535 | 7/1998 |
| WO | WO 98/45481 | 10/1998 |
| WO | WO 98/45929 | 10/1998 |
| WO | WO 98/46438 | 10/1998 |
| WO | WO 98/49548 | 11/1998 |
| WO | WO 98/55852 | 12/1998 |
| WO | WO 98/56956 | 12/1998 |
| WO | WO 99/00649 | 1/1999 |
| WO | WO 99/10735 | 3/1999 |
| WO | WO 99/12016 | 3/1999 |
| WO | WO 99/16162 | 4/1999 |
| WO | WO 99/19056 | 4/1999 |
| WO | WO 99/19516 | 4/1999 |

OTHER PUBLICATIONS

Schreiber et al.; "Portable, solid–state fluorometer for the measurement of chlorophyll fluorescence induction in plants"; *Rev. Sci. Instrum,* vol. 46, No. 5, May 1975, pp. 538–542.

Bruno et al.; "The pigtailing approach to optical detection in capillary electrophoresis"; *Trends in Analytical Chemistry,* vol. 13, No. 5 (1994), pp. 190–198.

Beach et al.; "A light–emitting diode light standard for photo– and videomicroscopy"; *Journal of Microscopy,* vol. 172, Pt. 1, Oct. 1993, pp. 41–48.

Kambara et al.; "Photodestruction of fluorophores and optimum conditions for trace DNA detection by automated DNA sequencer"; *Electrophoresis* 1992, 13, pp. 542–546.

Li, L–C. et al., "On–the–fly fluorescence lifetime detection of Labeled DNA primers" *J. Chromatog.* (1997) 695:85–92.

* cited by examiner

DNA SEQUENCING USING MULTIPLE FLUORESCENT LABELS BEING DISTINGUISHABLE BY THEIR DECAY TIMES

CROSS REFERENCE TO RELATED APPLICATIONS

This application is a continuation of U.S. Ser. No. 09/213,297, filed Dec. 15, 1998 now U.S. Pat. No. 6,447,724, entitled "DNA SEQUENCING USING MULTIPLE FLUORESCENT LABELS BEING DISTINGUISHABLE BY THEIR DECAY TIMES" by Morten J. Jensen and J. Wallace Parce, which was a non-provisional filing of 60/122,064, filed Aug. 11, 1998 now abandoned. The 60/122,064 application was converted by petition from regular U.S. utility filing U.S. Ser. No. 09/132,181 filed Aug. 11, 1998 now abandoned to the provisional 60/122,064 application. The present application claims priority to each of these prior applications, which are also incorporated herein by reference.

FIELD OF THE INVENTION

The present invention concerns the analysis of mixtures of compounds. More particularly, the present invention involves tagging individual compounds with unique fluorescent markers having different fluorescence lifetimes. The analysis of the mixture is then accomplished by distinguishing individual compounds by their unique fluorescence lifetime.

BACKGROUND OF THE INVENTION

In numerous fields, including organic chemistry, forensics, medical diagnosis and molecular biology there is a growing need for safe, efficient and cost-effective methods for identifying compounds of interest within a mixture of compounds. Mixtures of compounds frequently arise as the product of an organic synthetic cycle, during the isolation of a product of biological origin and during the chemical or enzymatic sequencing of polymeric compounds such as polypeptides, proteins, polysaccharides and nucleic acids.

Accurately determining nucleic acid base sequence is a prerequisite to further understanding the structure and function of the proteins produced by the encoded information. One such method, DNA sequencing, involves determining the order in which the nucleic acid bases are arranged within a length of DNA. Two DNA sequencing techniques which are widely known and in current use, are the chemical degradation procedure according to Maxam and Gilbert (*Proc. Natl. Acad. Sci. USA* 74:560 (1977)) and the enzymatic dideoxy chain termination method of Sanger et al (*Proc. Natl. Acad. Sci. USA* 74:5463 (1977)). Additionally, reference is made to, *Current Protocols in Molecular Biology*, F. M. Ausubel et al., eds., Current Protocols, a joint venture between Greene Publishing Associates, Inc. and John Wiley & Sons, Inc., (Supplement 37, current through 1997) (Ausubel), particularly, Chapter 7, which is incorporated herein by reference, for a description of DNA sequencing in general and various DNA sequencing techniques.

Traditional methods of DNA sequencing utilize a radiolabeled oligonucleotide primer to synthesize a nucleic acid having a sequence complementary to the sequence under analysis. Alternatively, a radiolabeled nucleotide is incorporated directly into the growing nucleic acid strand. Following synthesis, the radioactive nucleic acids are separated by a method such as gel electrophoresis and the positions of the nucleic acids are visualized by autoradiography. Although this technique provides sensitive detection, the use of radioisotopes and autoradiography requires extended exposure times and presents waste disposal problems.

Fluorescent-labeled oligonucleotide primers have been used in place of radiolabeled primers for sensitive detection of DNA fragments (U.S. Pat. No. 4,855,225 to Smith et al.). Additionally, DNA sequencing products can be labeled with fluorescent dideoxynucleotides (U.S. Pat. No. 5,047,519 to Prober et al.) or by the direct incorporation of a fluorescent labeled deoxynucleotide (Voss et al. *Nucl. Acids Res.* 17:2517 (1989)). As currently practiced, fluorescent sequencing reactions circumvent many of the problems associated with the use of radionuclides.

In an attempt to increase laboratory throughput and to further decrease exposure of laboratory workers to harmful reagents, various strategies have been developed. For example, robotic introduction of fluids onto microtiter plates is commonly performed to speed mixing of reagents and to enhance experimental throughput. More recently, microscale devices for high throughput mixing and assaying of small fluid volumes have been developed. For example, U.S. Ser. No. 08/761,575 entitled High Throughput Screening Assay Systems in Microscale Fluidic Devices by Parce et al. provides pioneering technology related to microscale fluidic devices, especially including electrokinetic devices. The devices are generally suitable for assays utilizing fluorophores which relate to the interaction of biological and chemical species, including enzymes and substrates, ligands and ligand binders, receptors and ligands, antibodies and antibody ligands, as well as many other assays. Because the devices provide the ability to mix fluidic reagents and assay mixing results in a single continuous process, and because minute amounts of reagents can be assayed, these microscale devices represent a fundamental advance for laboratory science.

The application of fluorogenic and non-fluorogenic assays utilizing fluorescent labels in flowing microfluidic systems are provided in Kopf-Sill et al. U.S. Ser. No. 09/093,542 "Apparatus and Methods For Correcting for Variable Velocity in Microfluidic Systems," filed Jun. 8, 1998. A fluorogenic assay is an assay in which a product of the assay emits a label distinct from those of the reactants of the assay. A non-fluorogenic assay is an assay in which the mobility of a product differs from those of labeled reactants (e.g., in a flowing electrokinetic system), but the emitted label is still the same as the label found on a reactant. Detection of non-fluorogenic assay products is possible in an electroosmotically driven microfluidic device using periodic injections of reaction mixture into a separation channel, in which reactants and products are separated by electrophoresis due to changes in the electrophoretic mobility resulting from the reaction (see also, A. R. Kopf-Sill, T. Nikiforov, L. Bousse, R. Nagel, & J. W. Parce, "Complexity and performance of on-chip biochemical assays," in Proceedings of Micro- and Nanofabricated Electro-Optical Mechanical Systems for Biomedical and Environmental Applications, SPIE, Vol. 2978, San Jose, Calif., February 1997, p. 172–179).

Closed-loop biochemical microfluidic devices especially adapted to sequencing nucleic acids, as well as for high-throughput screening are described in U.S. Ser. No. 09/054,962 entitled "Closed-loop Biochemical Analyzers" by Knapp et al., filed Apr. 3, 1998. In brief, in the integrated systems described, it is possible to use the results of a first sequencing reaction or set of sequencing reactions to select appropriate reagents, reactants, products, or the like, for additional analysis. For example, the results of a first sequencing reaction can be used to select primers, templates or the like for additional sequencing, or to select related families of compounds for screening in high-throughput assay methods. These primers or templates are then accessed by the system and the process continues.

Although sequencing and other assay methods that utilize fluorescent markers often represent, in many ways, an improvement over methods that utilize radioactive isotopes, current fluorescent methodologies are hampered by certain deficiencies. For example, in order to identify the individual nucleotides, each nucleotide must bear a fluorescent marker that has by a unique absorbance and/or emission spectrum with a different absorbance or emission maximum. Thus, to clearly distinguish the individual nucleotides based upon the fluorescence spectrum of their tags, the absorbance or emission maxima of each tag must be clearly resolved from those of every other tag. Further, fluorescence must be monitored at a number of different wavelengths in order to detect each of the maxima and a filtering system must be employed. This is cumbersome and increases the expense of the instrumentation. This situation is additionally complicated by the dependence of the absorption or emission maxima for a compound upon the environment surrounding that compound.

Thus, a method of detecting individual fluorescently labeled compounds within a mixture of compounds which relied on a characteristic of the fluorescent moiety other than its absorption and/or emission spectrum (e.g., maxima) would represent a significant advance in the art. The present invention provides such a method.

SUMMARY OF THE INVENTION

It has now been discovered that individual members of a mixture can be distinguished and identified through the selective use of a set of fluorescent labels displaying a range of unique fluorescence lifetimes. This method is versatile and it can be practiced with a wide range of separation modalities, fluorescent markers and labeling chemistries. Further, because it detects fluorescence lifetimes, rather than fluorescence emission or excitation maxima, this method is able to resolve a mixture containing several fluorescent species with overlapping fluorescent excitation and/or emission maxima.

Thus, in a first aspect, the present invention provides a method of distinguishing between a plurality of fluorescent species. The fluorescent species are first electrokinetically transported through a microfluidic channel. The fluorescent species are then excited by irradiating them with electomagnetic energy. The excitation can occur either during the transporting or at the completion of the transporting. Following this excitation, the fluorescent molecules are allowed to return to their ground state. This process is accompanied by a fluorescence emission which is characteristic for each fluorescent species and which is characterized by a temporal duration referred to as the fluorescence lifetime.

The lifetimes for each of the fluorescent labels is detected at a detecting station and the labeled species are identified by measuring the characteristic fluorescence lifetime of the label to which they are conjugated. It will be apparent to one of skill in the art that the present method can be practiced with any of an array of detecting station configurations. The detection station can include, for example, a laser or pulse lamp to excite the fluorescent species. Additionally, any useful configuration of lenses, prisms, mirrors, diffraction gratings, monochromators and the like can be used to practice the present invention. Useful detectors include fast, high sensitivity optical detectors like PMT, Avalanche Photo Diodes and Photo Diodes. The detector can be coupled to a digital computer that receives incoming data from the detector and processes it into a form useful for distinguishing between the lifetimes of the labels.

By detecting the fluorescence emission and measuring its lifetime for each of the fluorescent species in a mixture, the different fluorescent species present in the mixture can be detected and identified. Single or overlapping emissions that are composed of species with different lifetimes can be mathematically resolved into individual lifetimes, allowing the identification of the individual fluorescent constituents contributing to the emission.

The method is generally useful for the detection and identification of a broad range of compounds. It can be used to identify individual molecules which range in size and functionality from small organic, inorganic or organometallic molecules to proteins, including enzymes, antibodies and the like. The method of the invention can also be used to characterize and identify synthetic polymers and oligomers. These polymers and oligomers find utility in diverse fields of endeavor including, industrial applications, mechanical applications, drugs, foodstuffs and textiles. Synthetic, natural and modified polymers and oligomers of biomolecules such as amino acids, nucleic acids and saccharides can also be identified using the method of the invention.

Thus, in a second aspect, the present invention provides a method of sequencing a nucleic acid polymer of interest. In this aspect of the invention, the method comprises performing a sequencing reaction on the nucleic acid polymer. Any of the sequencing reactions known in the art is appropriate for use in this aspect. Thus, methods which chemically or enzymatically degrade or synthesize nucleic acids are of use in practicing the present invention.

During the course of the sequencing reaction, one or more fluorescent labels is incorporated into either the nucleic acid being sequenced or a sequence complementary to the nucleic acid being sequenced. Several methods for performing this incorporating are known in the art. A non-limiting list includes the Sanger, Sanger dideoxy and Maxam-Gilbert sequencing methodologies.

Sequencing reaction mixtures that are useful in practicing the present invention include those that contain the nucleic acid to be sequenced and a fluorescent label. The fluorescent label is attached to a first labeled nucleic acid selected from the group consisting of labeled nucleic acids, labeled nucleic acid polymers and combinations thereof. The fluorescent species are electrokinetically transported through a microfluidic channel to resolve or partially resolve the mixture into separate components.

As discussed above, the fluorescent label will, following excitation, emit electromagnetic energy that is characterized by a distinct and detectable lifetime. When more than one fluorescent label is utilized in the sequencing reaction mixture, each of the labels will have a fluorescent lifetime that is distinct from other labels and thereby detectable. The fluorescence emission is detected at a detecting station.

In addition to the above-described methods, the present invention also provides an apparatus that is particularly useful in practicing the methods of this invention. The apparatus is capable of distinguishing between a plurality of fluorescent species, wherein each of the fluorescent species has a fluorescence emission, the emission having a characteristic fluorescence lifetime.

The apparatus of the invention comprises a microfluidic device that contains at least one microchannel therein. The fluorescent species flows through the microchannel by means of, for example, electroosmosis, electrokinesis, capillarity and the like. The microchannel is linked to a detecting station that is capable of detecting the fluorescent species in the microchannel. The signal from the detector is sent to a digital computer that is operably linked to the detector. The digital computer is appropriately configured or programmed to determine the fluorescence lifetimes of the fluorescent species.

Other objects and advantages of the present invention will be apparent from the detailed description that follows.

DETAILED DESCRIPTION OF THE INVENTION AND THE PREFERRED EMBODIMENTS

Figure 1:
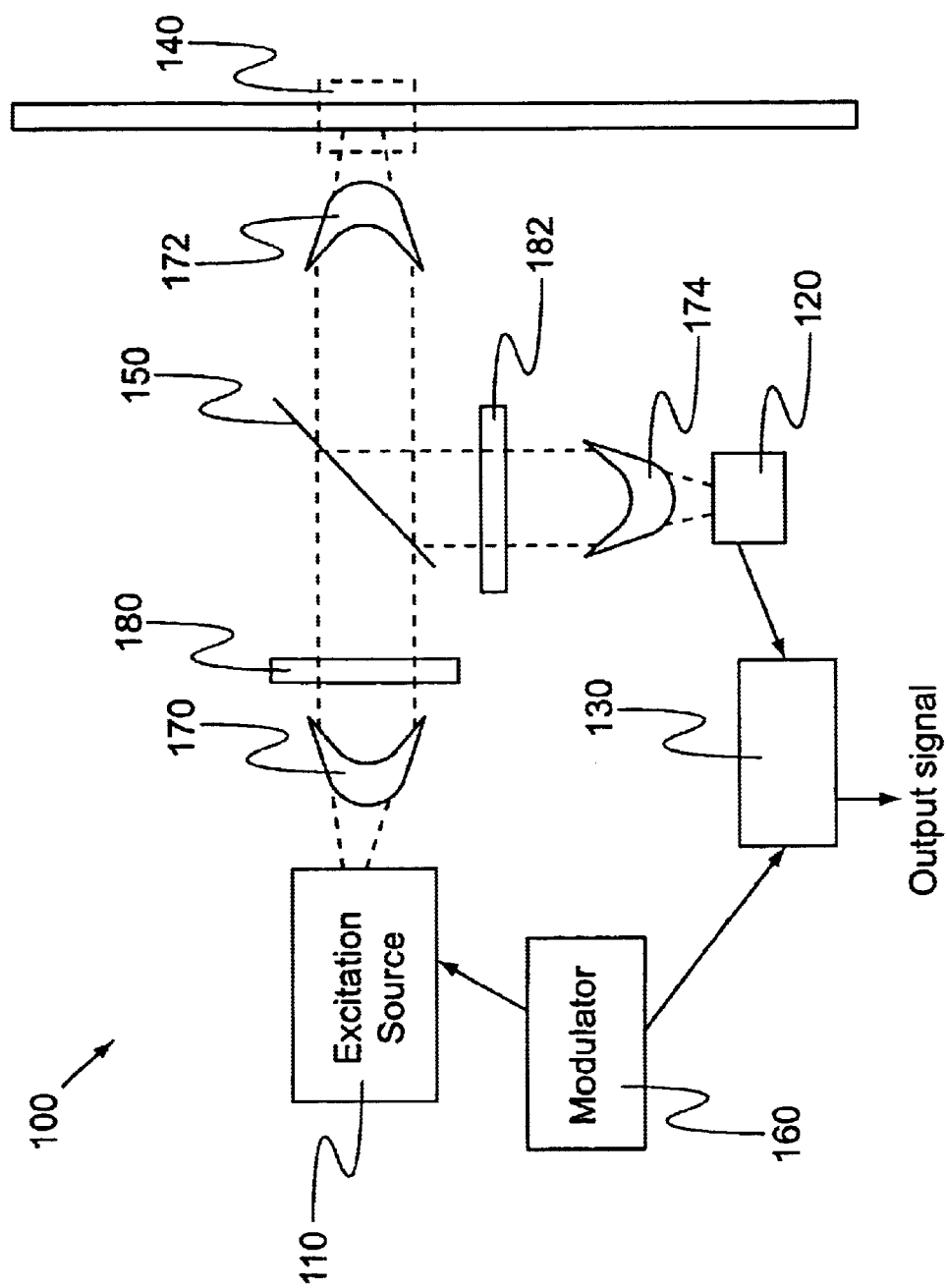
FIG. 1 is a block diagram of a fluorescence detection system of use in the present invention.

In a first aspect, the present invention provides a method of distinguishing between a plurality of fluorescent species. The fluorescent species are first electrokinetically transported through a microfluidic channel. The fluorescent molecules are then excited by irradiating them with electomagnetic energy. The excitation can occur either during the transporting or at the completion of the transporting. Following this excitation, the fluorescent molecules are allowed to return to their ground state. This process is accompanied by a fluorescence emission which is characteristic for each fluorescent species and which is characterized by a temporal duration referred to as the fluorescence lifetime of that species.

The lifetimes for each of the fluorescent labels is detected at a detecting station and the labeled species are identified by measuring the characteristic fluorescence lifetime of the label to which they are conjugated. It will be apparent to one of skill in the art that the present method can be practiced with any of an array of detecting station configurations. The detection station can include, for example, a laser or pulse lamp to excite the fluorescent species. Additionally, any useful configuration of lenses, prisms, mirrors, diffraction gratings, monochromators and the like can be used to practice the present invention. Useful detectors include fast, high sensitivity optical detectors like PMT, Avalanche Photo Diodes and Photo Diodes. The detector can be coupled to a digital computer that receives incoming data from the detector and processes it into a form useful for distinguishing between the lifetimes of the fluorescent labels.

By detecting the fluorescence emission and measuring its lifetime for each of the fluorescent species in a mixture, the different fluorescent species present in the mixture can be detected and identified. Single or overlapping emissions that are composed of species with different lifetimes can be mathematically resolved into individual lifetimes, allowing the identification of the individual fluorescent constituents contributing to the emission.

The individual members of virtually any complex mixture can be distinguished and identified using the method of the invention. Exemplary species include, for example, individual members of compound libraries (e.g., small organic molecules, peptides, nucleic acids) and the products of sequencing reactions. In a presently preferred embodiment, the method is used to distinguish between a plurality of fluorescent products derived from a sequencing reaction performed on a nucleic acid, a peptide or an oligosaccharide. In a further preferred embodiment, the fluorescent products are derived from a dideoxy nucleotide chain termination method sequencing reaction mixture derived from one or more nucleic acids. See, for example, Sanger et al., *Proc. Natl. Acad. Sci. USA* 74: 5463–5467 (1977); U.S. Pat. No. 5,171,534, to Smith et al. The means of practicing various embodiments of the present invention will be apparent from the theoretical and practical discussion that follows.

Fluorescence

A.1 Fluorescence Lifetime

The lifetime of a fluorescent molecule in an excited state is defined by the average time the molecule spends in the excited state prior to return to the ground state. Generally, fluorescence lifetime is described by Equation (1):

$$\tau = \frac{1}{\Gamma + k} \quad (1)$$

where $\tau$ is the fluorescence lifetime, $\Gamma$ is the emissive rate constant of the fluorophore and $k$ is the rate constant for radiationless decay.

As fluorescence emission is a random process, few molecules will emit their photons at $t=\tau$. The lifetime is merely an average value of the time spent in the excited state. For a single exponential decay, 63% of the molecules have decayed prior to $t=\tau$ and 37% decay at $t>\tau$.

The lifetime of a particular fluorophore, in the absence of nonradiative processes, is called the intrinsic lifetime, and is given in Equation (2):

$$\tau_0 = \frac{1}{\Gamma} \quad (2)$$

Thus the relationship between the quantum yield and the fluorescence lifetime for a particular molecule is given in equation (3):

$$Q = \frac{\tau}{\tau_0} \quad (3)$$

Both the quantum yield and the fluorescence lifetime can be modified by factors that affect either of the rate constants. For example, a molecule can be nonfluorescent as the result of a large rate of internal, radiationless conversion. In contrast, scintillation agents have high quantum yields. These high quantum yields are a result of high $\Gamma$ values relative to $k$.

A.2 Fluorophores

For the purpose of the invention, a fluorophore can be a substance which itself fluoresces, or can be made to fluoresce, or it can be a fluorescent analogue of an analyte. In principal, any fluorophore now known, or later discovered, can be used in the methods of the present invention.

Fluorescent species having lifetimes which fall within a broad range of measurable lifetimes are generally useful in the method of the present invention. In a presently preferred embodiment, the fluorescence lifetimes are from about 0.1 nanoseconds to about 4000 nanoseconds. In another preferred embodiment, the fluorescence lifetimes are from about 0.1 nanoseconds to about 1000 nanoseconds. In a still further preferred embodiment, the fluorescence lifetimes are from about 0.1 nanoseconds to about 100 nanoseconds.

Particularly preferred fluorophores have the following characteristics:

a. A fluorescence lifetime of greater than about 15 nanoseconds;

b. An excitation wavelength of greater than about 350 nanometers;

c. A Stoke's shift (a shift to longer wavelength of the emission relative to the absorption) of greater than about 20 nanometers; and d. The absorptivity and quantum yield of the fluorescence should be high.

The longer lifetime is advantageous because it is easier to measure and more easily distinguishable from the Raleigh scattering (background). Excitation wavelengths greater than 350 nanometers reduce the background interference because most fluorescent substances responsible for background fluorescence in biological samples are excited below 350 nanometers. A greater Stoke's shift also allows for less background interference.

Specific fluorescent compounds which are useful in practicing the present invention include, but are not limited to, dansyl, fluorescein, 8-anilino-1-napthalene sulfonate, pyrene, ethenoadenosine, ethidium bromide prollavine monosemicarbazide, p-terphenyl, 2,5-diphenyl-1,3,4-oxadiazole, 2,5-diphenyloxazole, p-bis[2-(5-phenyloxazolyl)]benzene, 1,4-bis-2-(4-methyl-5-phenyloxazolyl)-benzene, lanthanide chelates and derivatives of these compounds.

The only limitation on the choice of appropriate fluorescent compounds is that each compound in a set of fluorescent compounds used to analyze a mixture must have a fluorescence lifetime which, under relevant experimental conditions, is distinguishable from the fluorescence lifetimes of the other compounds in the set. Other appropriate fluorophores and combinations of fluorophores will be apparent to those of skill in the art.

In a preferred embodiment, the fluorophore is derivatized with a reactive functionality through which the fluorophore is tethered to a component of the mixture that is being analyzed. Many reactive fluorescent molecules are known by and readily available to those of skill in the art. Appropriate reactive fluorescent derivatives are commercially available (e.g., Molecular Probes Inc., Eugene, Oreg.) or they can be synthesized by means well known in the art.

Fluorescent agents that are reactive towards amines (e.g., isothiocyanates, carboxylic acids, succinimidyl esters, sulfonyl halides, dialdehydes), thiols (e.g., iodoacetamides, maleimides, alkyl halides, aziridines, epoxides, disulfides), alcohols (e.g., isocyanates, acylnitriles, acid chlorides), aldehydes, ketones, vicinal diols (e.g., hydrazine derivatives, amines) and carboxylic acids (e.g., amines, alkyl halides, trifluoromethansulfonates) are preferred for use in the present invention.

Before using the conjugates in the methods of the invention, models of the conjugates are preferably characterized as to spectral characteristics including optimal excitation and emission wavelength and fluorescence lifetime. All of these properties of the conjugates can be determined utilizing standard techniques. As the fluorescence lifetime of the conjugate may be dependent on the fluorophore to analyte ratio in the sample, the optimal ratio between the fluorophore and the analyte can be determined experimentally.

In choosing two or more fluorophores for use in the methods of the present invention, the following criteria pertain:

a. Ideally, the fluorophores should have substantial overlap of absorption bands so that they can be efficiently excited at a single wavelength;

b. The emission wavelengths should have substantial overlap of emission bands so that the fluorescence contribution of each label can be monitored at a single wavelength; and c. The differences in fluorescence lifetime between fluorophores should be at least 5 nanoseconds.

The use of a set of fluorescent compounds with overlapping emission bands allows the excitation of all of the compounds of the set to occur in a substantially simultaneous manner. In contrast, when the compounds are distinguished on the basis of the positions of their absorption bands, each member of the set of compounds must have a unique absorption band and each compound must be excited at a different wavelength.

When more than one fluorescent compound is used, a set of compounds which have substantially similar emission maxima are preferred. The use of a set of compounds having this characteristic allows the compounds to be detected and identified by monitoring their emission at one wavelength or within a narrow range of wavelengths.

In order to detect those compounds which are excited by, or which emit, electromagnetic energy at similar wavelengths, the compounds will preferably have lifetimes which are sufficiently different to allow them to be clearly distinguished. Thus, a useful set of compounds will include a group of compounds whose lifetimes differ from each other by at least 5 nanoseconds.

In view of the availability of an array of appropriate compounds, it is well within the capabilities of one skilled in the art to choose a reactive fluorescent molecule or set of molecules that is appropriate to the practice of the present invention. A broad range of appropriate fluorophores are commercially available from sources such as Molecular Probes Inc. (Eugene, Oreg.).

A.3 Measurement of Fluorescence Lifetimes

There are at least two widely used methods for the measurement of fluorescence lifetimes suitable for use in practicing the present invention. These are the pulse method and the phase-modulation method. In the pulse method, the sample is excited with a brief pulse of light and the time-dependant decay of fluorescence is measured. In the phase modulation method, the sample is excited with sinusoidally modulated light. The phase shift and demodulation of the emission, relative to the incident light, is used to calculate the fluorescence lifetime. Thus, in presently preferred embodiments, the detecting is provided by a pulse method or a phase-modulation method.

According to the method of this invention, all the fluorescence reaching the detector as a function of time from the instant of excitation is measured. Thus, the detected signal is a superposition of several signals (for example, background and one analyte-specific signal; or signals from different analytes in the case of multiple analyte assay, etc.). The individual contributions to the overall fluorescence reaching the detector are distinguished based on the different fluorescence decay rate (lifetime) of signal. The amplitude of a component of a signal is proportional to the specie responsible for the signal component.

Because of the ability of the method of the invention to distinguish between fluorophores on the basis of their different lifetimes, the position of the absorption, excitation and emission maxima are less relevant to the present technique than those techniques that make use of these maxima for compound identification, e.g., as described in U.S. Pat. No. 5,171,534, issued to Smith et al. Thus, in a preferred embodiment, the first fluorescent label and the second fluorescent label have an emission maximum that occurs at substantially the same wavelength. In some cases, however, additional resolution and/or complexity of analysis can be accomplished by using labels which have distinguishable excitation and/or emission maxima. Thus, in another presently preferred embodiment, the first fluorescent label and the second fluorescent label have an emission maximum that occurs at a substantially different wavelength.

A.3 a Detection Station

In accordance with this invention, individual compounds are identified at a detection station by stimulating and detecting their fluorescence and measuring the lifetime of the detected fluorescence. Useful detection stations will typically include three components, an excitation source, an optical system and a detector. Those of skill in the art will be able to choose, without undue experimentation, from a range of art recognized components and combinations of components to practice the present invention. See also, *The Photonics Design and Applications Handbook*, books 1, 2, 3 and 4, published annually by Laurin Publishing Co., Berkshire Common, P.O. Box 1146, Pittsfield, Mass. for common sources for optical components. Additional considerations for use of the present invention with microfluidic devices are discussed below.

A range of appropriate detection stations are available commercially. In a preferred embodiment, the detection station will use an excitation source which is a laser or a nanosecond flash lamp. Useful lasers include, but are not limited to, argon ion pumped and mode-locked Ti:sapphire lasers which provide tunable femto- or picosecond pulses. Suitable argon and mode-locked Ti:sapphire lasers are available as models INNOVA 420 and MIRA 900, respectively from the Laser Products Division of Coherent, Inc. (Palo Alto, Calif.). Other suitable lasers include Nd:YAG lasers such as models ANTARES 76-S, 468-ASE, 7950, 701 and 7049 from the Laser Products Division of Coherent, Inc. (Palo Alto, Calif.).

Nanosecond flash lamps that generate pulses on the nanosecond time-scale are commercially available. One suitable lamp is available from Photon Technology International (Monmouth Junction, N.J.) and generates pulses of 1.6 nanoseconds.

The optical system can be constructed to have any useful configuration known in the art and can comprise any number of lenses, mirrors, prisms, beam splitters and dispersive elements (e.g., monochronomators and diffraction gratings) and the like.

The detector can be any device that is capable of detecting photons including, but not limited to, photodiodes, photocathodes, photomultiplier tubes and the like. A presently preferred detector utilizes a stroboscopic detection system such as that described in James et al., *Rev. Sci. Instrum.* 63:1710 (1991).

The reactants or components to be detected after labeling with fluorescent labels distinguishable by their decay times can be elements of essentially any assay or reaction which is adaptable to a flowing or electrophoretic format; thus, while often described in terms of sequencing reactions, it will be understood that the reactants or assay components herein can comprise a moiety derived from any of a wide variety of components, including, antibodies, antigens, ligands, receptors, enzymes, enzyme substrates, amino acids, peptides, proteins, nucleosides, nucleotides, nucleic acids, organic molecules, monomers, polymers, drugs, polysaccharides, lipids, liposomes, micelles, toxins, biopolymers, therapeutically active compounds, molecules from biological sources, blood constituents, cells or the like. No attempt is made herein to describe how known assays utilizing these components are currently practiced. A wide variety of microfluidic assays are practiced using these components. See, e.g, WO 98/00231 entitled AHigh Throughput Screening Assay Systems in Microscale Fluidic Devices≠by Parce et al B. Sequencing Techniques B.1 Definitions As used herein, the term "DNA" or "deoxyribonucleic acid" shall be construed as collectively including DNA containing classical nucleotides, DNA containing one or more modified nucleotides (i.e., fluorescently tagged nucleotides containing a chemically modified base, sugar and/or phosphate), DNA containing one or more nucleotide analogs, and combinations of the above).

As used herein, the term "nucleotide" shall be construed as collectively including all of the forms of nucleotides described supra in addition to RNA and derivatives of RNA analogous to those of DNA discussed above.

As used herein the term "polymer" refers to molecules having two or more subunits (e.g., dinucleotides).

As used herein, the term "nucleic acid" is used interchangeably with RNA and DNA and this term can refer to monomeric, oligomeric or polymeric species of these molecules.

The methods and devices of the invention can also be utilized to sequence polymeric and oligomeric molecules including, but not limited to, DNA, RNA, peptides, polysaccharides and the like. In the interest of brevity, the discussion that follows focuses on techniques for sequencing nucleic acids. One of skill in the art will appreciate that with readily practiced modifications, the methods and apparatus of the invention can be utilized to sequence other polymeric molecules such as peptides, proteins, polysaccharides and the like.

Thus, in a second aspect, the present invention provides a method of sequencing a nucleic acid polymer of interest. In this aspect of the invention, the method comprises performing a sequencing reaction on the nucleic acid polymer to produce a nested set of sequence fragments. Any of the sequencing reactions known in the art is appropriate for use in this aspect. Thus, methods which chemically or enzymatically degrade or synthesize nucleic acids are of use in practicing the present invention. See, for example Maxam and Gilbert, *Proc. Natl. Acad. Sci. USA* 74: 560 (1977). When methods which synthesize nucleic acid polymers are utilized, a embodiment, involves producing a plurality of nucleic acid polymers complementary to a region of the nucleic acid polymer of interest. See, for example, Sanger et al., *Proc. Natl. Acad. Sci. USA* 74: 5463 (1977).

During the course of the sequencing reaction, one or more fluorescent labels is incorporated into either the nucleic acid being sequenced or a sequence complementary to the nucleic acid being sequenced. Several methods for performing this incorporation are known in the art. A non-limiting list includes the Sanger, Sanger dideoxy and Maxam-Gilbert sequencing methodologies. These methods are discussed in greater detail below.

Sequencing reaction mixtures that are useful in practicing the present invention include those that contain the nucleic acid to be sequenced and a fluorescent label. The fluorescent label is attached to a first labeled nucleic acid selected from the group consisting of labeled nucleic acids, labeled nucleic acid polymers and combinations thereof. As discussed above, the fluorescent label will, following excitation, emit electromagnetic energy that is characterized by a distinct and detectable lifetime. When more than one fluorescent label is utilized in the sequencing reaction mixture, each of the labels will have distinct and detectable fluorescence lifetimes.

Each of the above-enumerated sequencing methodologies can be used to practice the present invention. Those of skill in the art have ready access to a body of techniques for forming appropriate sequencing reaction mixtures for use in each of these methods. In a preferred embodiment, the sequencing reaction mixture further comprises a second labeled nucleic acid which is a member selected from the group consisting of labeled nucleic monomers and labeled nucleic acid polymers, wherein said nucleic acid bears a second fluorescent label. The second fluorescent label has a fluorescence emission that has a characteristic fluorescence lifetime.

In this embodiment, the second labeled nucleic acid can be a polymeric species such as an oligonucleotide (e.g., a primer or a dimer, trimer, etc.). When the nucleic acid is polymeric, the component bases of the polymer can be identical or they can be different over the length of the strand. Useful monomers include, for example, nucleotides, deoxynucleotides, dideoxynucleotides and modified derivatives thereof.

The second labeled nucleic acid can be an oligonucleotide primer that is used to start nucleic acid synthesis at a second region of the nucleic acid being sequenced. Alternatively, the second nucleic acid can also be a dideoxynucleotide such that chain elongation is terminated upon the dideoxynucleotide's incorporation into a growing nucleic acid.

In still further preferred embodiments, the sequencing reaction mixture further comprises additional labeled nucleic acids. The labels on these additional labeled nucleic acids will also have a fluorescence emission that has a characteristic fluorescence lifetime. It will be clear to one of skill in the art that any number of labeled nucleic acids can be used in a sequencing reaction mixture.

Thus, in certain nucleic acid sequencing procedures, more than four distinct nucleic acids will be present. In these embodiments, the first labeled nucleic acid bearing a first fluorescent label is a member of a plurality of unique labeled nucleic acid species. Similar to the above-described embodiments, the fluorescent label has a fluorescent emission that has a characteristic fluorescence lifetime.

Moreover, the set of labeled nucleic acids can include a mixture of nucleic acid species. For example, a sequencing reaction mixture can include a primer or a primer and one or more labeled dideoxynucleotides. Alternatively, another exemplary sequencing reaction mixture can include one or more labeled dideoxynucleotides and one or more deoxynucleotides with or without a primer present in the mixture. Other useful sequencing reaction mixture compositions will be apparent and readily accessible to those of skill in the art.

The method of the invention can be carried out by combining all of the labeled species in a "one pot" reaction or, alternatively, one or more of the labeled species can be segregated into one or more reaction vessels. In a presently preferred embodiment, the sequencing reaction is carried out with all of the fluorescently labeled species together as a mixture in a "one pot" reaction.

In another preferred embodiment, the sequencing reaction is performed following the Sanger procedure. See, for example, Sanger et al., *Proc. Natl. Acad. Sci. USA* 74: 5463 (1977). In this method, each of the labeled nucleic acids bearing a different fluorescent tag is incorporated into a polymeric nucleic acid. This embodiment can utilize a "one pot" reaction or, alternatively, one or more labeled species can be segregated and reacted in a separate reaction vessel. The labeled nucleic acids can be labeled primers, labeled deoxynucleotides, labeled dideoxynucleotides or combinations thereof.

In the embodiments which do not utilize a "one pot" reaction scheme, the method further comprises a second sequencing reaction mixture comprising the nucleic acid polymer of interest and a second labeled nucleic acid bearing a second fluorescent label, wherein the second fluorescent label has a fluorescence emission, the emission having a characteristic fluorescence lifetime.

When the nucleic acid to be sequenced contains more than two bases, additional sequencing mixtures can be optionally utilized. Thus, in yet another preferred embodiment, the method of the invention further comprises a third sequencing reaction mixture. Similar to the other sequencing reaction mixtures, the third sequencing mixture comprises the nucleic acid polymer of interest. The third sequencing reaction mixture also comprises a third labeled nucleic acid which is labeled with a third fluorescent label, wherein the third fluorescent label has a fluorescence emission which has a characteristic fluorescence lifetime.

In another preferred embodiment, the method of the invention further comprises a fourth sequencing reaction mixture that, similar to the mixtures discussed above, comprises a fourth labeled nucleic acid.

When two or more unique nucleic acid bases are present in a nucleic acid strand, in one embodiment, the present invention utilizes as many sequencing reaction mixtures as there are unique nucleic acid bases. In this embodiment, a particular sequencing reaction mixture is a member of a plurality of unique sequencing reaction mixtures. Each reaction mixture comprises the nucleic acid polymer of interest and a unique labeled nucleic acid bearing a unique fluorescent label, wherein the unique fluorescent label has a fluorescence emission. The emission has a characteristic fluorescence lifetime. The fluorescence lifetime is different for each unique fluorescent label.

In addition to the nucleic acid being sequenced, it will often be desirable or necessary to have one or more additional components in the sequencing mixture. The components can be chosen from a wide range of known enzymes, nucleic acids (e.g., labeled nucleic acids, labeled nucleic acid analogs, fluorescent labeled nucleic acids, oligonucleotides, etc.), solvents, buffers, catalysts, acids, bases, surfactants, chelating agents, metal ions and the like. Thus, in a presently preferred embodiment, the sequencing reaction mixture further comprises one or more members selected from the group consisting of polymerases, exonucleases, endonucleases, deoxynucleotides, deoxynucleotide diphosphates, deoxynucleotide triphosphates, dideoxynucleotides, dideoxynucleotide diphosphates, dideoxynucleotide triphosphates, nucleotide analogs and nucleoside analogs and combinations thereof.

When the method of the invention is used to sequence nucleic acids and the sequencing reaction mixture contains fluorescent labels and nucleic acids, it is preferred that the nucleic acids labeled with the fluorescent labels and that the nucleic acids are members selected from the group consisting of nucleotides, nucleosides, nucleoside diphosphates, nucleoside triphosphates, dideoxynucleosides, deoxynucleotides, deoxynucleoside diphosphates, deoxynucleoside triphosphates, dideoxynucleosides, dideoxynucleotides, dideoxynucleoside diphosphates, dideoxynucleoside triphosphates, nucleotide analogs and nucleoside analogs and combinations thereof.

Both natural and "unnatural" nucleotides can be derivatized with fluorescent labels and used to practice the present invention. Thus, in certain preferred embodiments, the nucleotide bearing a fluorescent label is a non-natural nucleotide.

In yet another preferred embodiment, the invention provides a sequencing reaction mixture as described above. In a still further preferred embodiment, the invention provides a kit comprising one or more sequencing mixtures as described above.

A number of nucleic acid sequencing techniques can be used in conjunction with the present invention. Broad classes of suitable sequencing techniques include those that use a chemical or enzymatic degradation process and those that use enzymatic synthesis of nucleic acids.

Methods that utilize chemical or enzymatic degradation of nucleic acids are known within the art and are suitable for use in practicing the present invention. See, for example, Ansorge et al., *Nucleic Acids Res.* 16:2203–2206 (1988); Porter et al. *Nucleic Acids Research* 25:1611–1617 (1997). Additionally, methods that utilize the enzymatic synthesis of nucleic acids can be used to practice the present invention including, for example, the Sanger method and its modifications. These methods are discussed in greater detail below.

B.2 Enzymes Used in DNA Sequencing

Two classes of enzyme activity that have been employed in certain methods used to sequence DNA are DNA polymerase and exonuclease activity. A DNA polymerase is an enzyme that has the ability to catalytically synthesize new strands of DNA in vitro. The DNA polymerase carries out this synthesis by moving along a preexisting single DNA strand ("the template") and creating a new strand complementary to the existing strand by incorporating single nucleotides one at a time into the new strand following the base-pairing rule.

In contrast to polymerase activity, exonuclease activity refers to the ability of an enzyme (an exonuclease) to cleave off a nucleotide at the end of a DNA strand. Enzymes are known which can cleave successive nucleotides off a single DNA strand, working from the 5' end of the strand to the 3' end; such enzymes are termed single-stranded 5' to 3' exonucleases. Other enzymes are known which perform this operation in the opposite direction (single-stranded 3' to 5' exonucleases). There also exist enzymes that can cleave successive nucleotides from the end of a single strand of a double-stranded DNA molecule. These enzymes are termed double-stranded 5' to 3' or 3' to 5' exonucleases, depending on the direction in which they proceed along the strand. Exonucleases are characterized as being distributive or processive in their action. Distributive exonucleases dissociate from the DNA following each internucleotide bond cleavage, whereas processive exonucleases will hydrolyze many internucleotide bonds without dissociating from the DNA.

Thermostable polymerases (e.g., Taq) are also useful in performing the polymerase chain reaction in conjunction with the sequencing method of the invention. See, for example, U.S. Pat. No. 4,683,202; Arnheim and Levinson, *C&EN* 36–47 (Oct. 1, 1990), Kwoh et al., *Proc. Nat'l. Acad. Sci. USA* 86:1173 (1989).

Thus, in yet another preferred embodiment, the method of the invention further comprises the use of the polymerase chain reaction to amplify the DNA being sequenced.

B.3 Sequencing Ladder Methods

Techniques for sequencing DNA generate fragments of labeled DNA, the lengths of which are sequence dependent, and separate the fragments according to their lengths, for example, by electric field induced migration in a gel or capillary. Such a pattern of sequence-dependent fragment lengths is known as a sequencing ladder.

When a nucleic acid is sequenced, by any of the above-discussed methods, the sequencing mixture will generally be submitted to a separation protocol that separates different populations of oligonucleotides on the basis of their size, charge, hydrophobicity and combinations of these properties. Thus, in a preferred embodiment, when an additive method such as the Sanger method is used, the method of the invention further comprises separating the complementary nucleic acid polymers into distinct populations, each of the populations consisting of nucleic acid polymers of about the same size.

Although any appropriate separation methodology can be utilized including, electrophoresis (gel, capillary, etc.), chromatography (HPLC, size exclusion, affinity, etc.), precipitation, and the like, in a presently preferred embodiment, the separating is provided by a method selected from the group consisting of electrophoresis, electroosmosis, electrokinesis, chromatography and combinations thereof.

The fragments of a sequencing ladder can be generated by either: (a) cleaving the DNA in a base-specific manner, or (b) synthesizing a copy of the DNA wherein the synthesized strand terminates in a base-specific manner.

The Maxam-Gilbert technique for sequencing involves the specific chemical cleavage of DNA. According to this technique, four samples of the same DNA are each subjected to a different chemical reaction to effect preferential cleavage of the DNA molecule at one or two nucleotides of a specific base identity. By adjusting the conditions to obtain only partial cleavage, DNA fragments are thus generated in each sample whose lengths are dependent upon the position within the DNA base sequence. Thus, after partial cleavage, each sample contains DNA fragments of different lengths each of which ends in the same one or two of the four nucleotides. See, Maxam and Gilbert, *Proc. Natl. Acad. Sci. USA* 74:560 (1977)

The plus/minus DNA sequencing method involves: (a) use of polymerases to generate complementary labeled DNA oligonucleotides of different lengths; (b) (the "minus" system) in four separate reaction vessels, reaction of one half of the generated DNA with DNA polymerase and three out of the four nucleotide precursors; (c) (the "plus system") in four separate reaction vessels, reaction of the remaining half of the generated DNA with DNA polymerase and only one of each of the four nucleotide precursors. Each reaction mixture generated in steps (b) and (c) is subjected to a separation procedure and the generated fragments are separated from each other by migration. See, Sanger and Coulson, *J. Mol. Biol.* 94:441–448 (1975).

The dideoxy method relies on the enzymatic activity of a DNA polymerase to synthesize DNA fragments with lengths that are sequence dependent. See, Sanger et al., *Proc. Natl. Acad. Sci. USA* 74:5463 (1977). The Sanger dideoxy method utilizes an enzymatically active fragment of the DNA polymerase termed *E. coli* DNA polymerase I, to carry out the enzymatic synthesis of new DNA strands. The newly synthesized DNA strands include fragments of sequence-dependent length, generated through the use of inhibitors of DNA polymerase which cause the base-specific termination of synthesis. Such inhibitors are dideoxynucleotides that, upon their incorporation by the DNA polymerase, destroy the ability of the enzyme to further elongate the DNA chain due to the dideoxynucleotides' lack of a suitable 3'-OH necessary in the elongation reaction. When a dideoxynucleotide whose base can appropriately hydrogen bond with the template DNA is thus incorporated into the DNA, synthesis of the growing polymer chain stops. Thus, DNA fragments are generated by the DNA polymerase, the lengths of which are dependent upon the position within the DNA base sequence of the nucleotide whose base identity is the same as the incorporated dideoxynucleotide. The fragments are then submitted to a separation procedure. For a simple introduction to dideoxy sequencing, see, *Current Protocols in Molecular Biology*, F. M. Ausubel et al., eds., Current Protocols, a joint venture between Greene Publishing Associates, Inc. and John Wiley & Sons, Inc., (Supplement 37, current through 1997) (Ausubel), Chapter 7. Four color sequencing is described in U.S. Pat. No. 5,171,534. Thousands of laboratories employ dideoxynucleotide chain termination techniques. Commercial kits containing the reagents most typically used for these methods of DNA sequencing are available and widely used.

Useful modifications to the Sanger method include, for example, the use of modified T7 DNA polymerase in two-step synthesis reactions as described in U.S. Pat. No. 4,994,372 to Tabor and Richardson and thermal stable DNA polymerases in two-step synthesis reactions as described in U.S. Pat. No. 5,075,216 to Brow et al. and thermal cycle DNA sequencing (Craxton, *Methods* 3:73–74 (1991)), all of which are incorporated herein by reference. The two-step labeling protocol and thermal cycle protocols employing thermostable DNA polymerases can be used to minimize problems associated with DNA template secondary structure.

The recent advent of thermal cycle sequencing methodologies has increased the number of suitable sequencing templates such as lambda and cosmid templates, polymerase chain reaction (PCR) products and direct plasmid sequencing from bacterial colonies. Because the thermal cycle methods employ heat denaturation, the requirement for alkaline denaturation and ethanol precipitation of double-stranded templates has been eliminated.

Current methods, prospects for automation and novel methods of DNA sequencing are reviewed by Martin and Davies (*Bio/Technology* 4:890–895 (1986)), Bains (*Bio/Technology* 8:1251–1256 (1990) and Hunkapiller et al. (*Science* 254:59 (1991)), which are incorporated herein by reference.

In addition to the Sanger methods of chain termination, new PCR exonuclease digestion methods have also been proposed for DNA sequencing. Direct sequencing of PCR generated amplicons by selectively incorporating boronated nuclease resistant nucleotides into the amplicons during PCR and digestion of the amplicons with a nuclease to produce sized template fragments has been proposed (Porter et al. *Nucleic Acids Research* 25:1611–1617 (1997)). In the methods, 4 PCR reactions on a template are performed, in each of which one of the nucleotide triphosphates in the PCR reaction mixture is partially substituted with a 2' deoxy-nucleoside 5'-[P-borano]-triphosphate. The boronated nucleotide is stocastically incorporated into PCR products at varying positions along the PCR amplicon in a nested set of PCR fragments of the template. An exonuclease which is blocked by incorporated boronated nucleotides is used to cleave the PCR amplicons. The cleaved amplicons are then separated by size using polyacrylamide gel electrophoresis, providing the sequence of the amplicon. An advantage of this method is that it requires fewer biochemical manipulations than performing standard Sanger-style sequencing of PCR amplicons.

Sequencing methods which reduce the number of steps necessary for template preparation and primer selection have been developed and can be applied to the present invention. One proposed variation on sequencing technology involves the use of modular primers for use in PCR and DNA sequencing. For example, Ulanovsky and co-workers have described the mechanism of the modular primer effect (Beskin et al., *Nucleic Acids Research* 23:2881–2885 (1995)) in which short primers of 5–6 nucleotides can specifically prime a template-dependent polymerase enzyme for template dependent nucleic acid synthesis. A modified version of the use of the modular primer strategy, in which small nucleotide primers are specifically elongated for use in PCR to amplify and sequence template nucleic acids has also been described. The procedure is referred to as DNA sequencing using differential extension with nucleotide subsets (DENS). See, Raja et al., *Nucleic Acids Research* 25:800–805 (1997).

In addition to enzymatic and other chain termination sequencing methods, sequencing by hybridization to complementary oligonucleotides has been proposed, e.g., in U.S. Pat. No. 5,202,231, to Drmanac et al. and, e.g., in Drmanac et al. *Genomics* 4:114–128 (1989). Chemical degradation sequencing methods are also well known and still in use; see, Maxam and Gilbert, *Methods in Enzymology* 65:499–560 (1980).

C. Sources of Nucleic Acids

Nucleic acids to serve as sequencing templates are optionally derived from a natural source or they can be synthetic or recombinant. For example, DNAs can be recombinant DNAs, e.g., plasmids, viruses or the like. A wide variety of molecular and biochemical methods are available for making coding DNAs. Examples of appropriate molecular techniques for generating recombinant nucleic acids, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); as well as in Sambrook, and Ausubel (both supra). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., Applied Biosystems (Foster City, Calif.), Digene Diagnostics, Inc. (Beltsville, Md.) as well as many other commercial sources known to one of skill.

Typically, oligonucleotides are used as sequencing primers, or as amplification primers. Most commonly, these DNA or RNA oligonucleotides are made synthetically. Synthetic oligonucleotides are typically synthesized chemically according to common solid phase phosphoramidite triester methods described, e.g., by Beaucage & Caruthers (1981) *Tetrahedron Letts.* 22(20):1859–1862, e.g., using an automated synthesizer, as described in Needham-VanDevanter et al. (1984) *Nucleic Acids Res.* 12:6159–6168. Oligonucleotides can also be custom made and ordered from a variety of commercial sources known to persons of skill. In other embodiments, oligonucleotides are made recombinantly according to standard techniques, described, e.g., in Berger, Sambrook and Ausubel, all supra.

Oligonucleotides are typically selected to have particular hybridization characteristics with a template DNA to form a duplex with the DNA. The oligonucleotide is typically used as a primer for a processive DNA polymerase in either a sequencing or amplification reaction. Most typically, oligonucleotides are selected to be fully complementary to the selected template DNA, although a portion of the oligonucleotide can be non-complementary (e.g., a portion may act as a labeling or cloning element instead of participating in hybridization, or a single oligonucleotide can be used as a primer for multiple closely related templates in separate assays to reduce individual assay costs). The oligonucleotides are preferably selected to have melting temperatures near the temperature of the reaction, to reduce background hybridization interactions. It is expected that one of skill is thoroughly familiar with the theory and practice of nucleic acid hybridization and selection of complementary oligonucleotides. See, e.g., Gait (ed.), OLIGONUCLEOTIDE SYNTHESIS: A PRACTICAL APPROACH, IRL Press, Oxford (1984); Kuijpers, *Nucleic Acids Research* 18(17):5197 (1994); Dueholm (1994) *J. Org. Chem.* 59:5767–5773; Agrawal (ed.) METHODS IN MOLECULAR BIOLOGY, volume 20; and Tijssen (1993) LABORATORY TECHNIQUES IN BIOCHEMISTRY AND MOLECULAR BIOLOGY-HYBRIDIZATION WITH NUCLEIC ACID PROBES, e.g., part I chapter 2; Overview of principles of hybridization and the strategy of nucleic acid probe assays, Elsevier, N.Y., provide a basic guide to nucleic acid hybridization. Most typically, oligonucleotide selection steps are performed using simple computer programs, although all of the steps are optionally performed manually. One available computer program for primer selection is the MacVector™ program from Kodak, or the MFOLD program (Genetics Computer Group, Madison Wis.).

D. Fluorescent Labeling of Nucleic Acids

Fluorescent tags useful in practicing the present invention can be tethered to any location on a nucleic acid, including sites on the base segment and sites on the sugar segment. Thus, in a preferred embodiment, the fluorescent label is covalently attached to a segment of a nucleic acid which is a member selected from the group consisting of the base segment, the sugar segment and both the base segment and the sugar segment.

In another preferred embodiment, the modified nucleic acid bears at least one fluorescent label and it serves as a primer for nucleic acid synthesis and the method of the invention further comprises annealing the nucleic acid polymer of interest with a primer nucleic acid polymer.

In another preferred embodiment, the fluorescent label is covalently attached to a labeled nucleic acid which is a member selected from the group consisting of the 3'-terminus, the 5'-terminus, an internal position and combinations thereof.

The art is replete with an arsenal of methods for the preparation, purification and characterization of a manifold of derivatized labeled nucleic acids. This subject has recently been reviewed. See, Goodchild, *Bioconjug. Chem.* 1:165–187 (1990), which is incorporated herein by reference.

Many of these methods are quite appropriate for use in preparing the various compounds required to practice the present invention. One skilled in the art will be able, without undue experimentation, to choose a suitable method for preparing a desired fluorescently labeled nucleic acid, oligonucleotide or the like. Additionally, as the art of organic synthesis, particularly in the area of nucleic acid chemistry, continues to expand in scope new methods will be developed which are equally as suitable as those now known. The following discussion is offered as representative of the array of compounds and techniques that can be used to modify nucleic acids. Methods useful in conjunction with the present invention, are not to be construed as limited by this discussion.

D.1 Modification of Intact Oligonucleotides

A number of techniques have been developed for converting specific constituents of DNA and RNA strands into fluorescent adducts. These techniques have been reviewed. See, Leonard and Tolman, in "Chemistry, Biology and Clinical Uses of Nucleoside Analogs," A. Bloch, ed., *Ann. N.Y. Acad. Sci.* 255:43–58 (1975).

Chemical methods are available to introduce fluorescence into specific nucleic acid bases by the reaction of chloracetaldehyde with adenosine and cytidine to give fluorescent products. The reaction can be controlled with respect to which of the two bases is derivatized by manipulating the pH of the reaction mixture; the reaction at 37° C. proceeds rapidly at the optimum pH of 4.5 for adenosine and 3.5 for cytidine. See, Barrio et al., *Biochem. Biophys. Res. Commun.* 46:597–604 (1972). This reaction is also useful for rendering fluorescent the deoxyribosyl derivatives of these bases. See, Kochetkov et al., *Dokl. Akad. Nauk. SSSR C* 213:1327–1330 (1973).

DNA and RNA can be modified by reacting their cytidine residues with sodium bisulfite to form sulfonate intermediates that are then coupled to reactive nitrogen compounds such as hydrazides or amines. See, Viscidi et al. *J. Clin. Microbiol.* 23:311 (1986) and Draper and Gold, *Biochemistry* 19:1774 (1980).

RNA can also be labeled at the 3' terminus by selective oxidation. The selective oxidation of the 3' ribose of RNA by periodate yields a dialdehyde which can then be coupled with an amine or hydrazide reagent. Churchich, *Biochim. Biophys. Acta* 75:274–276 (1963); Hileman et al. *Bioconjug. Chem.* 5:436–444 (1994).

Fluorescent G derivatives have also been prepared from the natural base upon its reaction with variously substituted malondialdehydes. See, Leonard and Tolman, in "Chemistry, Biology and Clinical Uses of Nucleoside Analogs," A. Bloch, ed., *Ann. N.Y. Acad. Sci.* 255:43–58 (1975).

D.2 De Novo Synthesis of Fluorescent Oligonucleotides

In addition to the various methods for converting the bases of an intact oligonucleotide into their fluorescent analogs, there are a number of methods for introducing fluorescence into an oligonucleotide during its de novo synthesis.

At least three methods are available for fluorescently tagging a synthetic oligonucleotide. These methods utilize fluorescently tagged supports, fluorescently tagged 5' modification reagents and fluorescently tagged monomers.

The first of these methods utilizes a fluorescently tagged linker that tethers the oligonucleotide strand to the solid support. When the oligonucleotide strand is cleaved from the solid support, the fluorescent tether remains attached to the oligonucleotide. This method affords an oligonucleotide that is fluorescently labeled at its 3'-end. In a variation on this method, the 3'-end of the nucleic acid is labeled with a linker that bears an amine, or other reactive or masked reactive group, which can be coupled to a reactive fluorophore following cleavage of the oligonucleotide from the solid support. This method is particularly useful when the fluorophore is not stable to the cleavage or deprotection conditions. An exemplary derivatized solid support is shown below in Formula I:

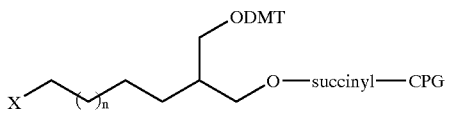

(I)

wherein n is an integer between 1 and 10 and X is a fluorophore or a reactive group such as, for example, NH$_2$, SH, OH, COOH, or a protected derivative of a reactive group. Methods for protecting these and other reactive groups are known in the art. See, for example, Greene and Wuts, PROTECTIVE GROUPS IN ORGANIC SYNTHESIS, 2$^{nd}$ Ed., John Wiley & Sons, N.Y., 1991.

A second method relies on the selective labeling of the 5' terminus of the oligonucleotide chain. Although many methods are known for labeling the 5' terminus, the most versatile methods make use of phosphoramidites which are derivatized with fluorophore or, if the fluorophore is unstable under the cleaving and deprotection conditions, a protected reactive functional group. The reactive functional group is labeled with a fluorophore following cleavage and deprotection of the oligonucleotide and deprotection of the reactive functional group.

The 5' derivatizing amidites are coupled to the growing nucleic acid strand as a last synthetic cycle that is generally accomplished in exactly the same manner as the previous steps that incorporated single nucleotides. An exemplary compound useful in this method is displayed below in Formula II:

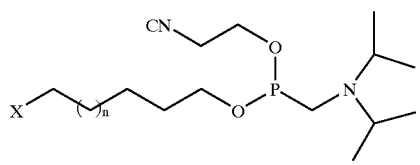

(II)

wherein n is an integer between 1 and 10 and X is a fluorophore or a reactive group such as, for example, NH$_2$, SH, OH, COOH, or a protected derivative of a reactive group.

Many reagents for effecting these conversions are commercially available from chemical houses such as Glen Research (Sterling, Va.). Other agents can be prepared de novo and the commercial agents can be modified by methods well known in the art.

D.3 Modified Labeled Nucleic Acids

Individual nucleotides can be derivatized with fluorescent moieties on the base or sugar components. Modification to the base can occur at exocyclic amines or at the carbons of the ring. See, for example, Levina et al., Bioconjug. Chem. 4:319–325 (1993). Modification of the sugar moiety can take place at the oxygens of the hydroxyl groups or the carbon atoms of the ribose ring. See, for example, Augustyns et al., Nucleic Acids Symp. Ser. 24:224 (1991); Yamana et al., Bioconjug. Chem. 7:715–720 (1996); Guzaev et al., Bioconjug. Chem. 5:501–503 (1994); and Ono et al., Bioconjug. Chem. 4:499–508 (1993), and references contained within, the disclosure of each of which is incorporated herein by reference.

The modified labeled nucleic acids can also be 2'-deoxyribonucleic acids which are labeled at the 3'-hydroxyl via, for example, alkylation or acylation. These labeled nucleic acids will function like dideoxynucleic acids, terminating synthesis, when used in the Sanger method.

As discussed above, fluorescent tags useful in practicing the present invention can be tethered to any location on a nucleic acid, including sites on the base segment and sites on the sugar segment. Thus, in a preferred embodiment, the fluorescent label is covalently attached to a segment which is a member selected from the group consisting of the base segment, the sugar segment and both the base segment and the sugar segment.

The methods and devices of the invention can be used to sequence nucleic acids of practically any length. In preferred embodiments, the nucleic acid lengths are within the art established ranges, preferably a size of from about 2 bases to about 100,000 bases, more preferably from about 100 bases to about 10,000 and still more preferably from about 300 bases to about 5000 bases.

The following exemplary embodiment illustrates a method of sequencing a nucleic acid using fluorescent labels and a chemical degradation pathway.

Fully protected oligodeoxyribonucleotides can be prepared on an Applied Biosystems DNA synthesizer using standard β-cyanoethyl phosphoramidite chemistry. See, Sinha et al., Nucleic Acids Res. 12:4539–4557 (1984). A portion of the material can be retained for a further synthetic cycle employing (S-trityl-3-mercaptopropyloxy), 2-cyanoethoxy N, N-diisopropylaminophosphine in the condensation step. This phosphoramidite has been synthesized and is known in the art. See, Ansorge et al., Nucleic Acids Res. 16:2203–6 (1988).

After removal of the blocking groups and cleavage from the support with ammonia, the S-trityl oligonucleotide can be purified by reverse-phase HPLC. Detritylation with silver nitrate and subsequent reaction of the liberated thiol with 5-iodoacetanidofluorescein can be performed as described in Ansorge et al., Nucleic Acids Res. 15:4593–4602 (1987). The excess dye can be removed by ethanol precipitations of the oligodeoxyribonucleotide. The fluorescein labeled oligodeoxyribonucleotide can be purified by reverse-phase HPLC, prior to sequencing by chemical degradation.

Chemical degradation of oligonucleotides can be performed essentially as described in Rosenthal et al., Methods Enzymol. 155:301–331 (1987) using Hybond M & G paper (Amersham). Approximately 5 pmol of fluorescein labeled oligomer can be applied to the carrier in 1 μl aliquots. For degradation, the following reagents can be used:

| | |
|---|---|
| G: | with 1% DMS in 50 mM ammonium formate buffer, pH 3.5 for 10 min.; |
| A + G: | with 80% formic acid for 20 min.; |
| T > Pu: | with 0.1 mM KMnO4 for 20 min,; |
| C: | with 4M hydroxylamine, pH 6. |

After piperidine reaction and lyophilization, the samples can be dissolved in 30% aqueous formamide.

In another exemplary embodiment, a lanthanide chelate serves as the fluorescent label. The chelate is diethylenetriaminepentaacetic acid (DTPA) and it is tethered to the nucleic acid using the corresponding DTPA dianhydride (DTPAA). In this embodiment, the method and device of the invention is used simply to separate and identify, not sequence, different oligonucleotides.

A plasmid, such as plasmid pBR322 is purified and digested according to art-recognized procedures. See, Mamatis et al. MOLECULAR CLONING: A LABORATORY MANUAL, Cold Springs Harbor Laboratory, Cold Springs Harbor, N.Y., pp. 100–106. The digestion of pBR322 generates 10 fragments with staggered ends ranging from 75 base pairs to 1631 base pairs; the sequence of single-stranded bases at each end is ANT, where N denotes any nucleotide. It is assumed that the exocyclic amines on the exposed bases provide sites for attachment of the DTPA moiety via amide linkages formed between these amines and a carboxylate group of the DTPA.

The DTPAA is added to the plasmid digest and stirred at room temperature for at least 60 minutes. After storage overnight at 4° C. a lanthanide salt (e.g., terbium chloride) is added to the reaction mixture. The resulting mixture is shaken and allowed to stand for at least 30 minutes. Excess hydrolyzed chelate and lanthanide salt can be separated from the plasmid digest-chelate conjugate by passing the mixture through a column packed with Sephadex, such as Sephadex G 25–150. Suitable elution buffers include, for example, 10 mM 3-[N-morpholino]propane sulfonic acid at pH 7. The DNA fractions can then be pooled and evaporated to dryness. The DNA fractions can then be loaded into a microfluidic device and sequenced.

The plasmid digest-chelate conjugate can be characterized by determining the DNA concentration by measuring the absorbance at 260 nm. Label concentration can be determined by comparing the fluorescence of the purified labeled nucleotide conjugate with the fluorescence of the free chelate complexed with terbium. Suitable instrumentation for these measurements includes a Perkin-Elmer Lambda Array UV-Vis spectrometer and a Perkin-Elmer LS-5 spectrofluorimeter.

Other exemplary methods of attaching fluorescent labels onto nucleic acids are taught in U.S. Pat. No. 5,721,355 and Chehab and Kan, *Proc. Nat'l. Acad. Sci. USA* 86:9178–9182 (1989).

E. Microfluidic Devices

As discussed above, any of a number of methods and devices are suitable for use in the present invention for separating the components of a mixture, however, typically, the methods of the invention are practiced in the context of a microfluidic system. Fluorescently labeled components (typically multiple components comprising one or more labels distinguishable by their decay time) are transported through a microfluidic channel. Material transport and direction in the microfluidic channel is typically accomplished through electrokinesis, e.g., electroosmosis or electrophoresis, although micropumps and miniature mechanical valves can also be used.

Thus, in a preferred embodiment, the separating is performed using a microfluidic apparatus. A preferred microfluidic apparatus has a substrate with at least two intersecting channels fabricated into its surface. The channels preferably have at least one cross-sectional dimension that is in the range of from about 0.1 to about 500 µm.

In other preferred embodiments, when a sequencing reaction is used, in certain preferred embodiments, the sequencing reaction is performed using the microfluidic device. The microfluidic device also comprises a detecting station and the device is used for both separating and detecting the components of a mixture.

In yet a further preferred embodiment, the microfluidic device is also used for identifying the compounds of the mixture by the differences in their fluorescence lifetimes. In this embodiment, the invention provides a microfluidic device with at least one microchannel, a detector for detecting fluorescence species in the channel and a digital computer which is operatively linked to the detector. The digital computer is used to determine the lifetimes of the fluorescent species.

As used herein, "electrokinetic material transport systems" or "electrokinetic devices" include systems which transport and direct materials within an interconnected channel and/or chamber containing structure, through the application of electrical fields to the materials, thereby causing material movement through and among the channel and/or chambers, i.e., cations will move toward the negative electrode, while anions will move toward the positive electrode. Such electrokinetic material transport and direction systems include those systems that rely upon the electrophoretic mobility of charged species within the electric field applied to the structure. Such systems are more particularly referred to as electrophoretic material transport systems. For electrophoretic applications, the walls of interior channels of the electrokinetic transport system are optionally charged or uncharged. Typical electrokinetic transport systems are made of glass, charged polymers, and uncharged polymers. The interior channels are optionally coated with a material which alters the surface charge of the channel.

Other electrokinetic material direction and transport systems rely upon the electroosmotic flow of fluid and material within a channel or chamber structure which results from the application of an electric field across such structures. In brief, when an appropriate fluid is placed in a channel or other fluid conduit having functional groups present at the surface, those groups ionize. For example, where the surface of the channel includes hydroxyl functional groups at the surface, protons can leave the surface of the channel and enter the fluid. Under such conditions, the surface will possess a net negative charge, whereas the fluid will possess an excess of protons or positive charge, particularly localized near the interface between the channel surface and the fluid. By applying an electric field along the length of the channel, cations will flow toward the negative electrode. Movement of the positively charged species in the fluid pulls the solvent with them. An electrokinetic device moves components by applying an electric field to the components, in a microfluidic channel. By applying an electric field along the length of the channel, cations will flow toward a negative electrode, while anions will flow towards a positive electrode. Movement of charged species in the fluid pulls the solvent with the fluid, provided the fluid is mobile. In pure electrophoretic applications, elements of the fluid are not mobile, e.g., due to cross-linking, i.e., where the fluid is a gel matrix, or due to a lack of surface charge on the walls of the interior channel.

The steady state velocity of fluid movement is generally given by the equation:

$$v = \frac{\varepsilon \xi E}{4\pi \eta}$$

where v is the solvent velocity, $\varepsilon$ is the dielectric constant of the fluid, $\xi$ is the zeta potential of the surface, E is the electric field strength, and $\eta$ is the solvent viscosity. The solvent velocity is, therefore, directly proportional to the surface potential.

To provide appropriate electric fields, the system generally includes a voltage controller that is capable of applying selectable voltage levels, simultaneously, to each of the reservoirs, including ground. Such a voltage controller can be implemented using multiple voltage dividers and multiple relays to obtain the selectable voltage levels. Alternatively, multiple independent voltage sources are used. The voltage controller is electrically connected to each of the reservoirs via an electrode positioned or fabricated within each of the plurality of reservoirs. In one embodiment, multiple electrodes are positioned to provide for switching of the electric field direction in a microchannel, thereby causing the analytes to travel a longer distance than the physical length of the microchannel. Use of electrokinetic transport to control material movement in interconnected channel structures was described in WO 96/04547 to Ramsey, which is incorporated by reference.

Modulating voltages are concomitantly applied to the various reservoirs to affect a desired fluid flow characteristic, e.g., continuous or discontinuous (e.g., a regularly pulsed field causing the flow to oscillate direction of travel) flow of labeled components toward a waste reservoir. Particularly, modulation of the voltages applied at the various reservoirs can move and direct fluid flow through the interconnected channel structure of the device in a controlled manner to effect the fluid flow for the desired screening assay and apparatus.

Typically, the microfluidic systems of the invention provide an integration of several elements, including a microfluidic device with interior microfluidic channels and reservoirs, optics for viewing labeled components, computer systems and software for recording and analyzing components and the like. WO 98/00231 entitled "High Throughput Screening Assay Systems in Microscale Fluidic Devices" by Parce et al. provides pioneering technology related to microscale fluidic devices, especially including electrokinetic devices. The devices are generally suitable for assays relating to the interaction of biological and chemical species, including enzymes and substrates, ligands and ligand binders, receptors and ligands, antibodies and antibody ligands, as well as many other assays. Because the devices provide the ability to mix fluidic reagents and assay mixing results in a single continuous process, and because minute amounts of reagents can be assayed, these microscale devices represent a fundamental advance for laboratory science. Pioneering integrated systems for nucleic acid sequencing and other iterative fluid manipulation processes utilizing microfluidic fluid manipulation are described in, e.g., U.S. provisional patent application Serial No. 60/068,311, entitled "Closed Loop Biochemical Analyzer" by Knapp, filed Dec. 19, 1997 and "Closed Loop Biochemical Analyzers" by Knapp et al. U.S. Ser. No. 09/854,962 filed Apr. 3, 1998.

In the integrated systems provided by Knapp, pioneering iterative methods, including nucleic acid sequencing methods as applied to microfluidic systems are described in detail. These systems are applicable to the present invention, i.e., by using the systems to produce sequencing reaction products and then measuring fluorescent decay times of sequencing products as described supra. In these embodiments, standard primer walking sequencing strategies are automated and integrated. All of the mixing and analysis steps for sequencing are optionally performed with an integrated system. In brief, a template nucleic acid is selected and introduced into a reaction channel in a microfluidic device of the invention. The template is optionally amplified, e.g., by introducing PCR or LCR reagents into the channel and performing cycles of heating and cooling on the template. Thermocycling in microscale devices is described in co-pending application U.S. Ser. No. 60/083,532, entitled "Electrical Current For Controlling Fluid Temperatures In Microchannels" filed Apr. 29, 1998 by Calvin Chow, Anne R. Kopf-Sill and J. Wallace Parce and in related application Ser. No. 08/977,528, filed Nov. 25, 1997. In brief, energy is provided to heat fluids, e.g., samples, analytes, buffers and reagents, in desired locations of the substrates in an efficient manner by application of electric current to fluids in microchannels. Thus, the present invention optionally uses power sources that pass electrical current through the fluid in a channel for heating purposes, as well as for material transport. In exemplary embodiments, the fluid passes through a channel of a desired cross-section (e.g., diameter) to enhance thermal transfer of energy from the current to the fluid. The channels can be formed on almost any type of substrate material such as, for example, amorphous materials (e.g., glass, plastic, silicon), composites, multi-layered materials, combinations thereof, and the like.

Alternatively, e.g., where the source of template is from an abundant sequence such as a cloned nucleic acid, further amplification can be unnecessary. In addition to amplification procedures, a PCR nuclease chain termination procedure can also be used for direct sequencing in the methods of the invention, by incorporating fluorescent nucleotides which are distinguishable by their decay time into templates for sequencing. Porter et al. (1997) Nucleic Acids Research 25(8):1611–1617 describe the biochemistry of PCR chain termination methods.

Sequencing reagents are added to the template nucleic acid and a sequencing reaction is performed appropriate to the particular reaction in use. Many appropriate reactions are known, with the Sanger dideoxy chain termination method being the most common. In integrated systems, the primer used to prime synthesis is optionally selected from a pre-synthesized set of nucleic acid primers, preferably a set including many or all of the primers for a particular primer length. In one aspect, modular primers are used. See, Beskin et al. (1995) Nucleic Acids Research 23(15):2881–2885 and Raja et al. (1997) Nucleic Acids Research 25(4):800–805 for a description of modular primers. See, Knapp et al., supra for a description of the use of modular primers in microfluidic systems. These primers can incorporate fluorescent labels distinguishable by their decay times, or nucleotides incorporated by primer extension can incorporate such labels.

After the sequencing or other reaction is run, products are separated by size and/or charge in an analysis region of the microfluidic device. Devices of the invention can be used to electrophoretically separate macromolecules by size and/or charge. The separated products are detected as they pass a fluorescent detector (nucleic acids and other molecules are typically labeled with fluorophores that are distinguishable by their decay times in the present invention; accordingly, appropriate detectors include spectrophotometers, fluorescent detectors, microscopes (e.g., for fluorescent microscopy), etc. As applied to the present invention, the detection systems are adapted to measure fluorescence decay times.

In sequencing reactions, detection of the size separated products is used to compile sequence information for the region being sequenced. A computer is optionally used to select a second primer from the pre-synthesized primer set which hybridizes to the sequenced region, and the process is iteratively repeated with the second primer, leading to sequencing of a second region, selection of a third primer hybridizing to the second region, etc. A variety of commercially available hardware and software is available for digitizing, storing, and analyzing a signal or image such as that generated by the microfluidic device described herein. Typically, a computer commonly used to transform signals from the detection device into reaction rates will be a PC™-compatible computer (e.g., having a central processing unit (CPU) compatible with x86 CPUs, and running an operating system such as DOS™, OS/2 Warp™, WINDOWS/NT™, or WINDOWS 95™), a Macintosh™ (running MacOS™), or a UNIX workstation (e.g., a SUN™ workstation running a version of the Solaris™ operating system, or PowerPC™ workstation) are all commercially common, and known to one of skill in the art. Data analysis software on the computer is then employed to determine the rate of formation and or mobility of any component which is labeled with a fluorescent label distinguishable by its decay time. Software for determining reaction rates is available, or can easily be constructed by one of skill using a standard programming language such as Visual Basic, Fortran, Basic, Java, C, Visual C++ or the like. It will be recognized that the specific configuration of integrated devices and systems will generally vary depending upon the type of manipulation or reaction to be performed. The small scale, integratability and self-contained nature of the microfluidic elements of these devices and systems allows for virtually any reaction or separation to be performed.

Finally, it should be appreciated that the use and detection of fluorescent labels which are distinguishable by their decay times can be applied in microfluidic systems to a variety of problems other than sequencing. Essentially any fluorogenic or non-fluorogenic assay can be practiced using fluorescent labels which are distinguishable by their decay times. Kopf-Sill et al. U.S. Ser. No. 09/093,542 "Apparatus and Methods For Correcting for Variable Velocity in Microfluidic Systems," filed Jun. 8, 1998 which provides a variety of fluorogenic and non-fluorogenic assay formats for microfluidic systems. See also, A. R. Kopf-Sill, T. Nikiforov, L. Bousse, R. Nagel, & J. W. Parce, "Complexity and performance of on-chip biochemical assays," in *Proceedings of Micro-and Nanofabricated Electro-Optical Mechanical Systems for Biomedical and Environmental Applications*, SPIE, Vol. 2978, San Jose, Calif., February 1997, p. 172–179). These include a variety of reactants and products assessed in microfluidic systems by detection of fluorescent or non-fluorescent labels, including ligands and ligand binders such as an antibody and an antibody ligand, receptors and receptor ligands, biotin and avidin, proteins and complementary binding proteins, carbohydrates and carbohydrate binding moieties, nucleic acids, etc.

In brief, reactants or molecules which hybridize are contacted by flowing the components together in a microfluidic system. At least one of the components is typically labeled with a label distinguishable by its decay time. Products and reactants are detected and quantitated by observing, e.g., the movement of labels in the system. Data correction for the effects of velocity of components can be applied, e.g., by considering conservation of flux in the flowing systems, by generating and applying data masking files, by using self-correcting fluid sampling techniques and the like. See, Kopf-Sill et al. supra.

Preferred arrangements for electrokinetic movement and monitoring of fluorescent decay times are described in "Methods and Systems for Sequencing DNA by Distinguishing the Decay Times of Fluorescent Probes".

In brief, FIG. 1 is a block diagram of a fluorescence detection system 100 according to an embodiment of the present invention. Detection system 100 includes excitation source 110 for exciting fluorophores in detection region 140 with an excitation signal, and detector 120 for detecting fluorescence emission signals from detection region 140. Fluorescence detector 120 is coupled to processor 130 which analyzes signals from fluorescence detector 120 to determine fluorescence lifetimes. Beamsplitter element 150, positioned between excitation source 110 and detection region 140, is optionally provided to allow a substantial portion of the excitation signal incident from excitation source 110 to pass through to detection region 140, and to redirect a substantial portion of the radiation incident from detection region 140, including fluorescence emissions, toward fluorescence detector 120. Modulator 160 is provided to modulate excitation source 110 to obtain the desired excitation signal characteristics. For example, in one embodiment, modulator 160 includes an oscillator that generates a reference signal having a desired frequency and amplitude. In this embodiment, excitation source emits radiation having a time-dependent intensity, e.g., sinusoidally modulated light, in response to the reference signal. In another embodiment, modulator 160 includes a pulse generator that pulses excitation source 110. Alternatively, an electro-optical chopping device (not shown), located between excitation source 110 and detection region 140, can also be used to physically chop a continuous excitation signal into a series of pulses as is well known.

In preferred aspects, excitation source 110 is a radiation source that emits radiation having a wavelength in the range of about 300 nm to about 800 nm, and which is modulated with a reference signal having a frequency in the range of about 1 MHz to about 100 MHz. More preferably, excitation source 110 is a laser diode that emits visible radiation having a wavelength of approximately 635 nm, and which is modulated at approximately 10 MHz. Modulator 160 is provided according to this embodiment to modulate the excitation source at the desired frequency and amplitude to obtain the desired excitation signal characteristics. One of skill in the art will, of course, be able to determine other suitable modulation frequencies and characteristics without undue experimentation depending on the particular characteristics of the fluorophores being analyzed. Other suitable excitation sources include any radiation source that emits, or which can be controlled to emit, radiation pulses or radiation having a time-dependent intensity, such as a laser, a flashlamp, a light emitting diode (LED), an arclamp, or the like.

In one embodiment, fluorescence detector 120 includes a photo multiplier tube (PMT) that measures fast light signals with low intensity and outputs a corresponding proportional signal to processor 130. Fluorescence detector 120 must be fast enough to convert the fluorescence emission signal into a proportional electrical signal. Therefore, fluorescence detector 120 must operate at a rate faster than the decay times of the particular fluorophores being distinguished. Alternatively, fluorescence detector 120 can include an avalanche photo diode or a photodiode, or any other light detection device that measures fast light signals at low intensity and outputs a proportional signal to processor 130. Additionally, as PMTs tend to decrease in efficiency as the wavelength of detected light increases, in some embodiments where fluorescence emissions in the red to infrared wavelengths are to be detected the use of an avalanche photodiode is preferred.

Fluorescence detection system 100 also includes additional optical elements for enhancing the excitation and detection capabilities of system 100. Optical elements 171 and 172, positioned between excitation source 110 and detection region 140, are optionally provided according to one embodiment to assist in directing and focusing the excitation signal onto detection region 140. Optical elements 170 and 172 can include focusing lenses, mirrors, or any other optical elements as are well known and which are useful for collimating, directing and focusing radiation depending on the desired system layout and characteristics. Optical element 174 is optionally provided in one embodiment to assist in directing and focusing the fluorescence emissions signals from detection region 140 onto fluorescence detector 120. Optical element 174 in one embodiment includes a focusing lens selected accordingly depending on whether fluorescence emission signals are received by fluorescence detector 120 directly from detection region 140 or via reflection from beamsplitter element 150.

Filter elements 180 and 182 are optionally provided to avoid an overlap of the excitation source spectra and the detectable fluorescence emission spectra. Additionally, filter element 180 can be used to prevent undesirable wavelengths, other than the desired excitation wavelength, that may also be emitted by excitation source 110 from irradiating detection region 140. Filter element 182 can be used to filter unwanted background noise (light) and fluorescence emissions from certain solid support materials in the detection region, e.g., microchannel capillary tubes and the like. An electronic filter can also be used to filter out background noise and unwanted fluorescence emissions from the fluorescence signal received by fluorescence detector 120. In one embodiment, the signal from detector 120 is electronically filtered so that only the emitting frequency (e.g., 10 MHz) is detected. The resulting signal can then be compared to the modulation reference signal to determine the fluorescence lifetimes or to determine which is the dominating fluorescence lifetime.

In operation, excitation signals (e.g., pulses or sinusoidally varying) from excitation source 110 irradiate detection region 140 and excite fluorophores therein, thereby causing the fluorophores to fluoresce. Fluorescence detector 120 detects the resulting fluorescence emissions, either directly or by reflection from beamsplitter element 150, and generates a proportional signal. Processor 130 receives and analyzes the signal from fluorescence detector 120, which is proportional to the overall fluorescence emissions signal received by fluorescence detector 120 from detection region 140. In one embodiment, processor 130 is coupled to modulator 160. In this embodiment, processor 130 receives a reference signal from modulator 160, which is proportional to the reference signal used to modulate excitation source 110. Processor 130 can use this reference signal as a reference for determining the fluorescence lifetimes from the signal received from fluorescence detector 120. If the excitation source emits, or is modulated to emit, excitation pulses, the processor measures the decay time directly; if the excitation source emits, or is modulated to emit, a sinusoidally varying excitation signal, the processor determines the fluorescence lifetimes by measuring the phase difference or the demodulation relative to the excitation modulation reference signal. A phase-locked loop (PLL) is preferably used to determine phase differences and/or demodulation. It is not necessary that processor 130 be able to quantify each fluorophore, but, rather that it is able to categorize and distinguish each fluorophore effectively. For example, when used to sequence a nucleic acid in a prepared nucleic acid sample that is separated in an electrophoretic gel transported across detection region 140, processor 130 determines the nucleotide sequence by the relative characteristics of the fluorescent decay times of the different fluorescent labels or labels used.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications are incorporated herein by reference.

What is claimed is:

1. A method of distinguishing between a plurality of fluorescent species, wherein each of said fluorescent species has a fluorescence emission, said emission having a characteristic fluorescence lifetime, said method comprising:

(a) transporting each of said fluorescent species through a microfluidic channel;

(b) detecting each of said fluorescent species in said channel; and, (c) identifying each of said fluorescent species by measuring said characteristic flourescence lifetime, wherein at least a first fluorescent species and a second fluorescent species have characteristic fluorescence lifetime that differ by at least about 5 nanoseconds.

2. A method of distinguishing between a plurality of fluorescent species; wherein each of said fluorescent species has a fluorescence emission, said emission having characteristic fluorescence lifetime, said method comprising (a) transporting each of said fluorescent species through a microfluidic channel;

(b) detecting each of said fluorescent species in said channel; and (c) identifying each of said fluorescent species by measuring said characteristic fluorescence lifetime, and (d) contacting said plurality of fluorescent species with one or more sequencing reagents in said microfluidic channel, thereby performing a sequencing reaction.

3. The method of claim 2, wherein the one or wore sequencing reagent is selected from one or more of; a nucleic acid polymer, a nucleic acid template, nucleic add primer, a fluorescently labeled nucleic acid, a polymerase, an exonuclease, an endonuclease, a metal ion, a chelating agent, surfactant, an acid, a base, a solvent, a buffer and a catalyst.

4. The method of claim 2, wherein performing the sequencing reaction comprises producing a plurality of nucleic acid polymers complementary to a region of a nucleic acid template, the method further comprising electrokinetically separating the plurality of nucleic acid polymers prior to stop (b).

5. A method of sequencing a nucleic acid, the method comprising:

(a) introducing the nucleic acid into a microfluidic device;

(b) contacting the nucleic acid with a plurality of sequencing reagents, thereby performing a sequencing reaction resulting in a plurality of fluorescently labeled nucleic acid sequence fragments, wherein each of said fragments has a fluorescence emission, said emission having a characteristic fluorescence lifetime;

(c) electrokinetically separating said fragments;

(d) detecting each of said fragments in said microfluidic device; and, (e) identifying each of said fragments by measuring said characteristic fluorescence lifetime, thereby sequencing the nucleic acid.

6. The method of claim 5, wherein the plurality of sequencing reagents comprises a nucleic acid primer, a polymerize, and one or more fluorescent species selected from: a nucleotide, a nucleoside, a dideoxynucleoside, dideoxynucleotide, a deoxynucleoside, a deoxynucleotide, a nucleotide analog, and a nucleoside analog.

* * * * *